US00PP17510P3

(12) United States Plant Patent
Grech et al.

(10) Patent No.: US PP17,510 P3
(45) Date of Patent: Mar. 20, 2007

(54) LIMONEIRA SEEDLESS

(50) Latin Name: *Citrus limon*
Varietal Denomination: Limoneira Seedless

(75) Inventors: Nigel Grech, Reedley, CA (US); Ercan Ekenler, Tarsus (TR)

(73) Assignee: Limoneira Company, Santa Paula, CA (US)

( * ) Notice: Subject to any disclaimer, the term of this patent is extended or adjusted under 35 U.S.C. 154(b) by 40 days.

(21) Appl. No.: 11/044,284

(22) Filed: Jan. 26, 2005

(65) Prior Publication Data

US 2006/0179523 P1 Aug. 10, 2006

(51) Int. Cl.
*A01H 5/00* (2006.01)

(52) U.S. Cl. ..... Plt./201

(58) Field of Classification Search ..... Plt./201
See application file for complete search history.

(56) References Cited

U.S. PATENT DOCUMENTS

PP4,828 P 3/1982 Harjung et al.

*Primary Examiner*—Kent L. Bell
(74) *Attorney, Agent, or Firm*—Mark D. Miller

(57) ABSTRACT

A new and distinct cultivar of seedless lemon tree named 'Limoneira Seedless' characterized by early bearing in August through to March in the inland citrus areas of South East Turkey and Riverside, Calif. The trees can be induced to flower by irrigation stress in summer, resulting in a late spring crop of lemons. It is further characterized by being commercially seedless. The fruit has acceptable rind thickness, acid-sugar ratios and color. The skin has a smooth texture. The fruit has an average juice content of 30–40% at harvest. The fruit shape is typically round to slightly oval elliptical.

12 Drawing Sheets

*Citrus limon.*
Variety denomination: 'Limoneira Seedless'.

BACKGROUND OF THE NEW VARIETY

The present invention refers to a new variety of lemon which will hereinafter be denominated as the 'Limoneira Seedless' lemon tree. The 'Limoneira Seedless' tree produces commercially seedless lemon fruit, bearing in August through to March in the inland citrus areas of South East Turkey and Riverside, Calif. The 'Limoneira Seedless' trees can be induced to flower by irrigation stress in the summer, resulting in production of a late spring crop of lemons. The skin has a smooth texture. The fruit has acceptable rind thickness, acid-sugar ratios and color, and has an average juice content of 30–40% at harvest.

In the development of new commercial fruit varieties, specific characteristics provide a premium on those fruit varieties that mature early or late in the growing season. In general, early varieties tend to lack size, flavor and color. Therefore in order for a fruit to be a commercial success, the fruit must be of good size, good color, and also have good holding/storage and shipping characteristics. In addition, the date of maturing must be different from other similar fruit. This new invention meets all of the aforementioned criteria and therefore would be of commercial appeal to the consumer.

ORIGIN AND ASEXUAL REPRODUCTION OF THE NEW VARIETY

The invention (variety) comprises a new and distinct variety of a seedless lemon plant named 'Limoneira Seedless'. The new cultivar is a selection from an old line nucellar block of unknown parentage, but probably the result of a hybrid between a 'Femminello' group lemon and the 'Interdonato' lemon varieties. The selection was discovered in 1998 by the inventors in Adana, Turkey (approximately 350° E, 370° 15' N). The new cultivar was subsequently asexually reproduced by the inventors in 1999 by bud grafting on to 'Sour Orange' root stock (200 trees in total). The resulting trees were experimentally evaluated. The resulting tree growth was medium to strong with no bud union abnormalities being noted on the 'Sour Orange' rootstock. An additional 10 trees were asexually reproduced by the inventors in 2003 by bud grafting on to 'Sour Orange' root stock and grown in Riverside, Calif. The inventors carefully compared all of the asexually reproduced trees with the originally discovered tree including the fruit and found they are identical in all respects. The instant tree reproduces true to type in successive generations of such asexual reproductions.

SUMMARY OF THE NEW VARIETY

The 'Limoneira Seedless' is particularly characterized by being commercially seedless and an early bearing variety, maturing when grown in the inland citrus areas of southeast Turkey. The season for the 'Limoneira Seedless' lemon in southeastern Turkey and Riverside, Calif. is from August to March. In comparison, the season for the locally grown lemon 'Kutiken' lemon (unpatented) in southeastern Turkey is November to February, and that of the 'Interdonato' (unpatented) in southeastern Turkey is September to February. The acid to sugar ratios and the juice content for the 'Limoneira Seedless' are similar to commercially grown lemons. The trees exhibit acceptable tolerance to cold and to the malady known as Mal secco, a fungal disease of serious importance in the Mediterranean citrus regions.

DETAILED DESCRIPTION

Referring more specifically to the horticultural details of the new and distinct variety of lemon trees, the following descriptions have been observed on a $4^{th}$ year tree under the ecological conditions prevailing at the origin orchard which is located in Adana, Turkey, as well as in Riverside, Calif. Color references are to the Dictionary of Color by Maerz and Paul, First Edition published in 1930. Common colors are also employed.

TREE

Size: Medium, for $4^{th}$ year tree.
*Height.*—10 feet.
*Width.*—10 feet at drip line.
Shape: Upright, effuse growth habit when grown on Sour Orange rootstock.
Growth: Dense; vigorous branches tend to grow out, upward beyond trees' general periphery; abundant axillary and accessory bud development.
Vigor: Medium to strong.
Productivity: Very good for $4^{th}$ year tree with regular bearing; fruit produced predominantly inside the canopy resulting in less fruit scaring.

TRUNK

Immediately above the rootstock interface on sour orange:
Size: Circumference of 12–16 inches, 18 inches above ground.
Surface texture: Smooth.
Color: 4 year old tree, Andover green (23-E-2).
Lenticels: Many.

BRANCHES

Figure 9:
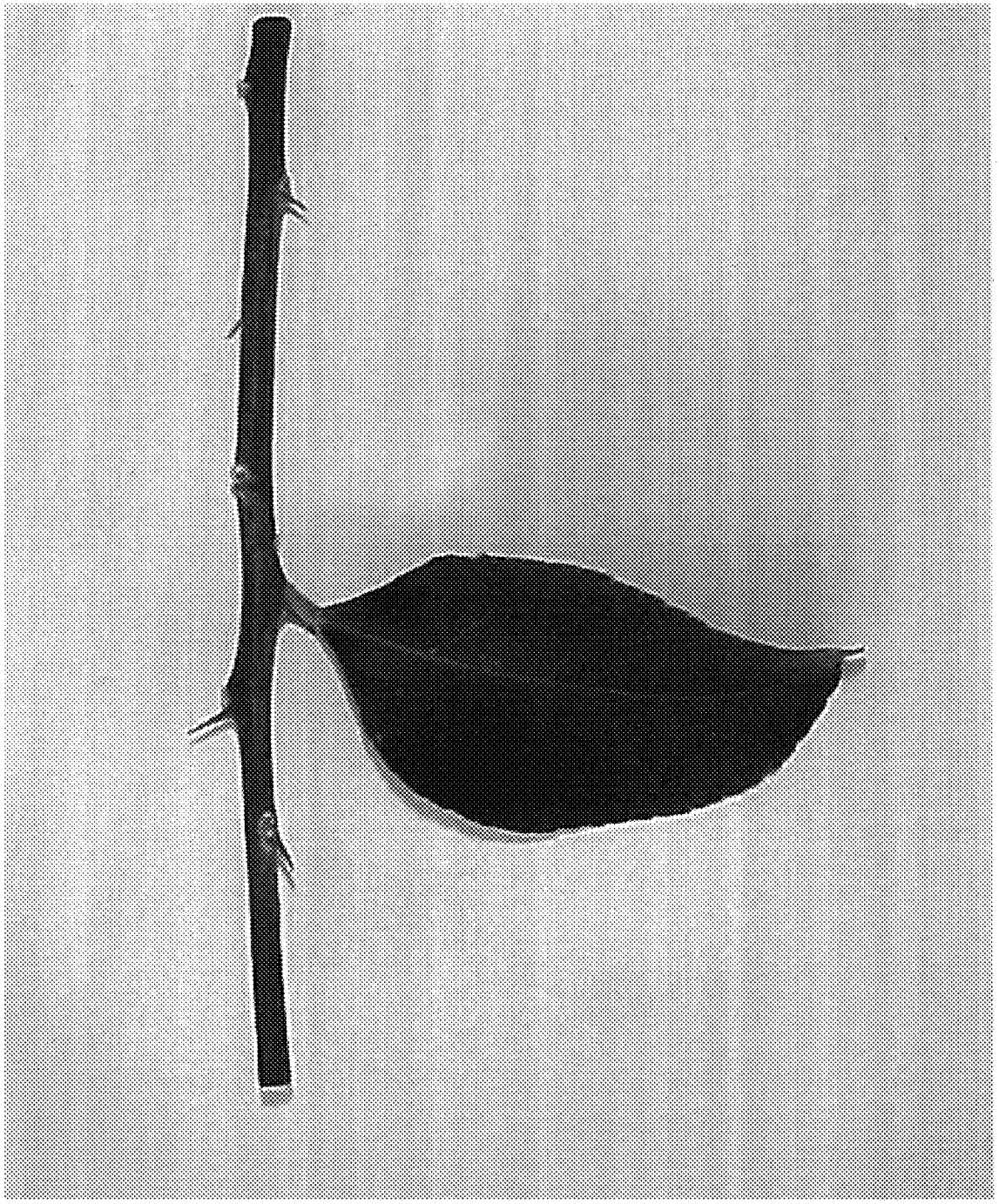
FIG. 9 is a color photograph showing of a branch of the present invention with small thorns.

Size: Scaffold (structural) branches, circumference of 10–12 inches; Secondary branches (on which fruit bearing branches are borne) circumference of 4–6 inches.
Angle of branches extending from main trunk: Average between about 30° and about 50°.
Color of branches over 2 years old: Andover green (23-E-2).
Color of branches less than 2 years old: Brunswick green, $LT^P$ (22-L-10).
Thorns: Persistent during growth but are reduced in number as the tree ages. On grafted trees the branches have small thorns particularly evident during the first three years. The thorns are on the apical side of the leaf petiole. See FIG. 9.
*Number.*—9–12 thorns per foot on branches less than 2 years old; 0–6 thorns per foot on branches over 2 years old.
*Size length.*—8–10 mm (0.32–0.4 in.).
*Width at base.*—2–3 mm (0.08–0.12 in.). A typical observed thorn has an average length of about 9 mm (0.36 in) and an average width at the base of about 2.5 mm (0.1 in.).

LEAVES

The leaves are alternate, unifoliate with distinct articulation between the petiole and leaf blade. They exhibit a distinctly curvate morphology with undulation, and are without basal wings.

Size: Medium.
*Length.*—75–100 mm (2.95–3.94 in.).
*Width.*—50–60 mm (1.97–2.36 in.).
Texture: Smooth.
Shape: Elliptically oval to oblong.
Margin: Serrated.
Apex: Mild crenation to rounded.
Base: Narrowed.
Edges: Distinctly smoother towards the basal leaf end.
Marginal oil cells: Many 12 per linear cm; oil cells are ovoid and raised.
Color: Mature leaves glossy.
*Upper surface.*—Wintergreen English ivy + (23-A-12).
*Lower surface.*—Fern (21-I-7).
*Petioles.*—No wings (characteristic of true lemon).
*Length.*—Less than 7–12 mm (0.28–0.48 in.).
*Diameter.*—Less than 3 mm (0.12 in.).
*Color.*—Apple green (19-J-6).
Venation: Distinct, pinnately reticulated.
Midvein: Width at base, 1–2 mm (0.04–0.08 in.); Width at apex, 0.3 mm–0.4 mm (0.012–0.016 in.). Color: Wintergreen English ivy + (23-A-12).

FLOWERS

The flowers are large and complete. Flower buds have pink anthocyanin coloration during early development, but lose the pigmentation by anthesis. Flowers are borne in multiple clusters and have an average number of stamens (about 20) with complete style development. Anther color is pale yellow to yellow. Pollen fertility is low as indicated by the observation that only 3–5% of the pollen grains were stained with acetocarmine in a test conducted on this variety. The flowers have a sweet pleasing citrus fragrance.

Flower buds:
*Shape.*—10 days prior to anthesis, slightly ovoid, 10 mm (0.4 in.) diameter; 1–2 days prior to flowering, elongated cone, 10 mm (0.4 in.) diameter, 20 mm (0.8 in.) length.

Calyx: 4–5 sepals, fused forming a cup-like calyx.

*Exterior surface color.*—Calliste green (19-L-6). Lobe tips are blunt but with apiculate tips.

Date of normal first bloom: Southeast Turkey: First bloom: about March 15$^{th}$; end bloom about April 15$^{th}$ Riverside, Calif.: First bloom about April 1$^{st}$, end bloom about April 20$^{th}$.

Figure 1:
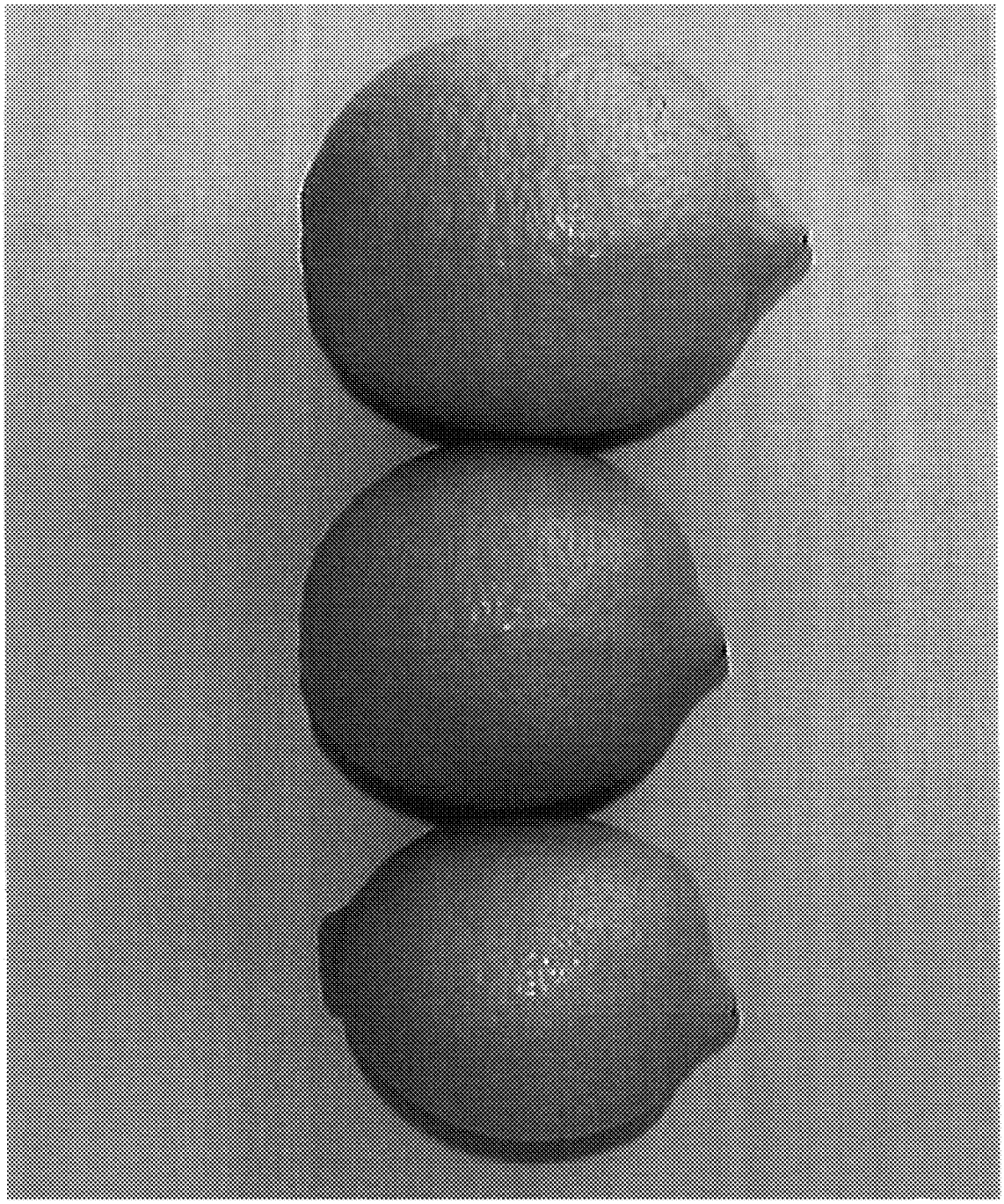
FIG. 1 is a color photograph showing a front perspective view of three specimens of typical whole fruit of the present invention harvested in November 2002.
Figure 2:
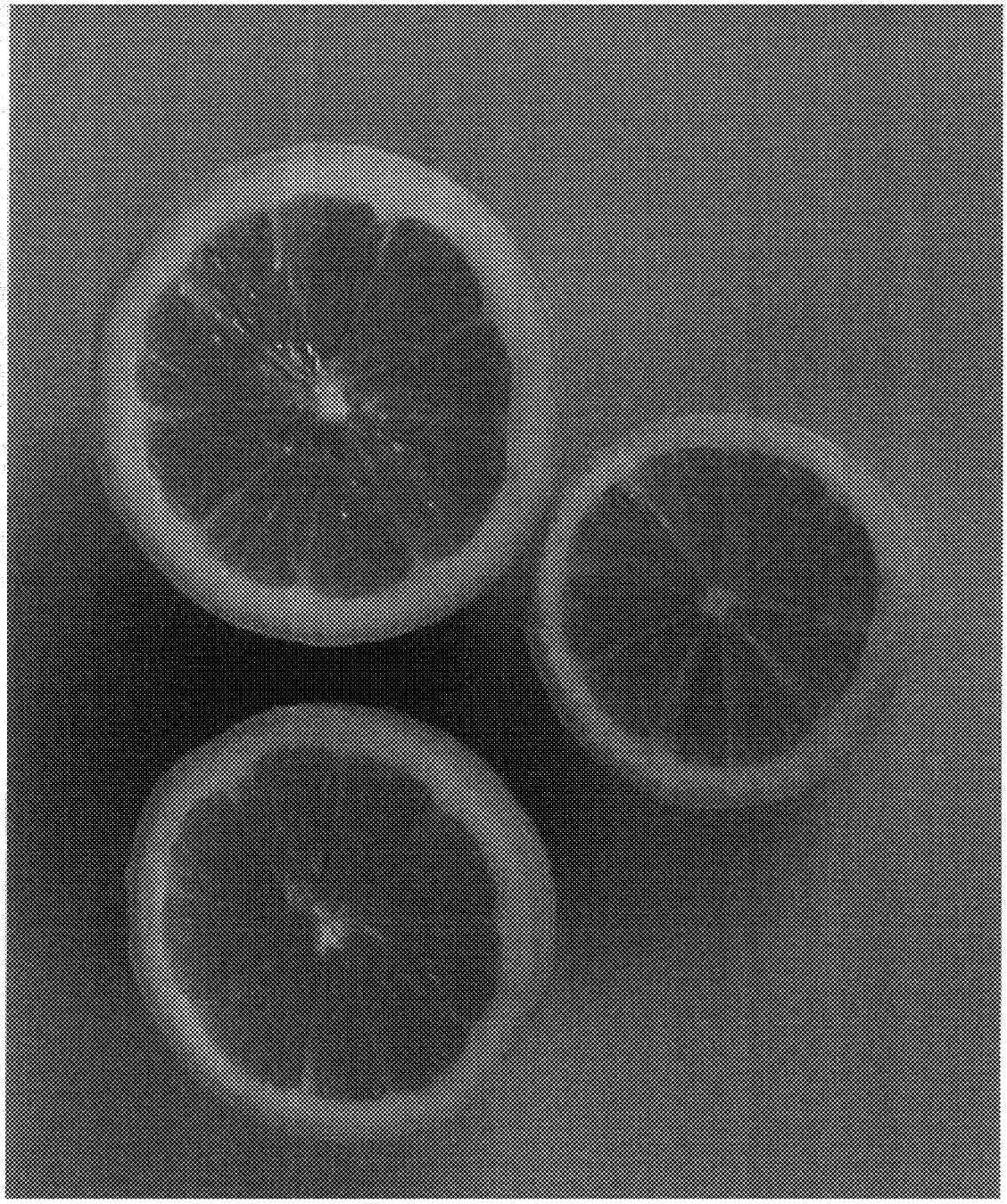
FIG. 2 is a color photograph showing a typical transverse cut section of the fruit of FIG. 1.
Figure 3:
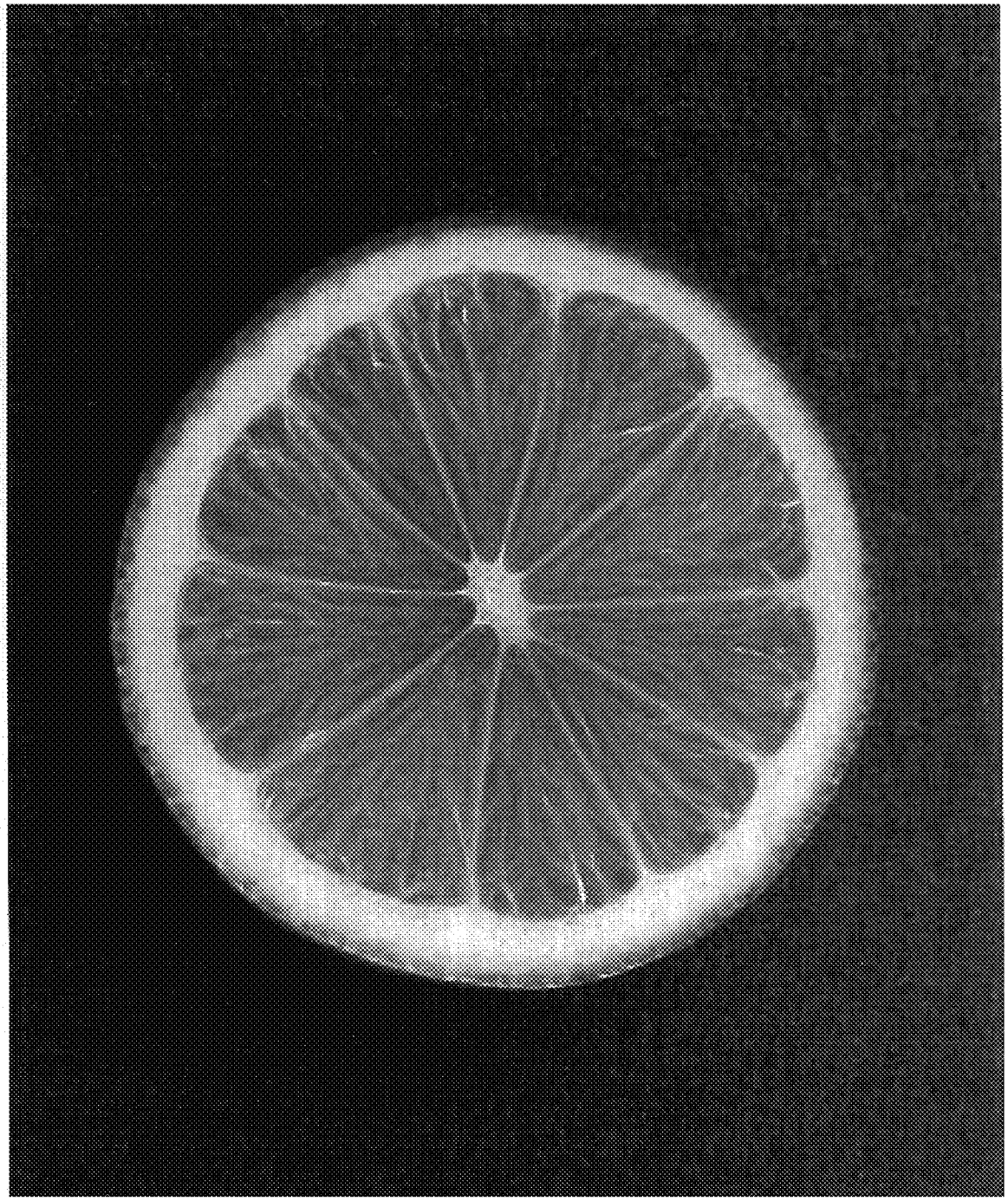
FIG. 3 is a color photograph showing another typical transverse cut section of fruit of the present invention.
Figure 4:
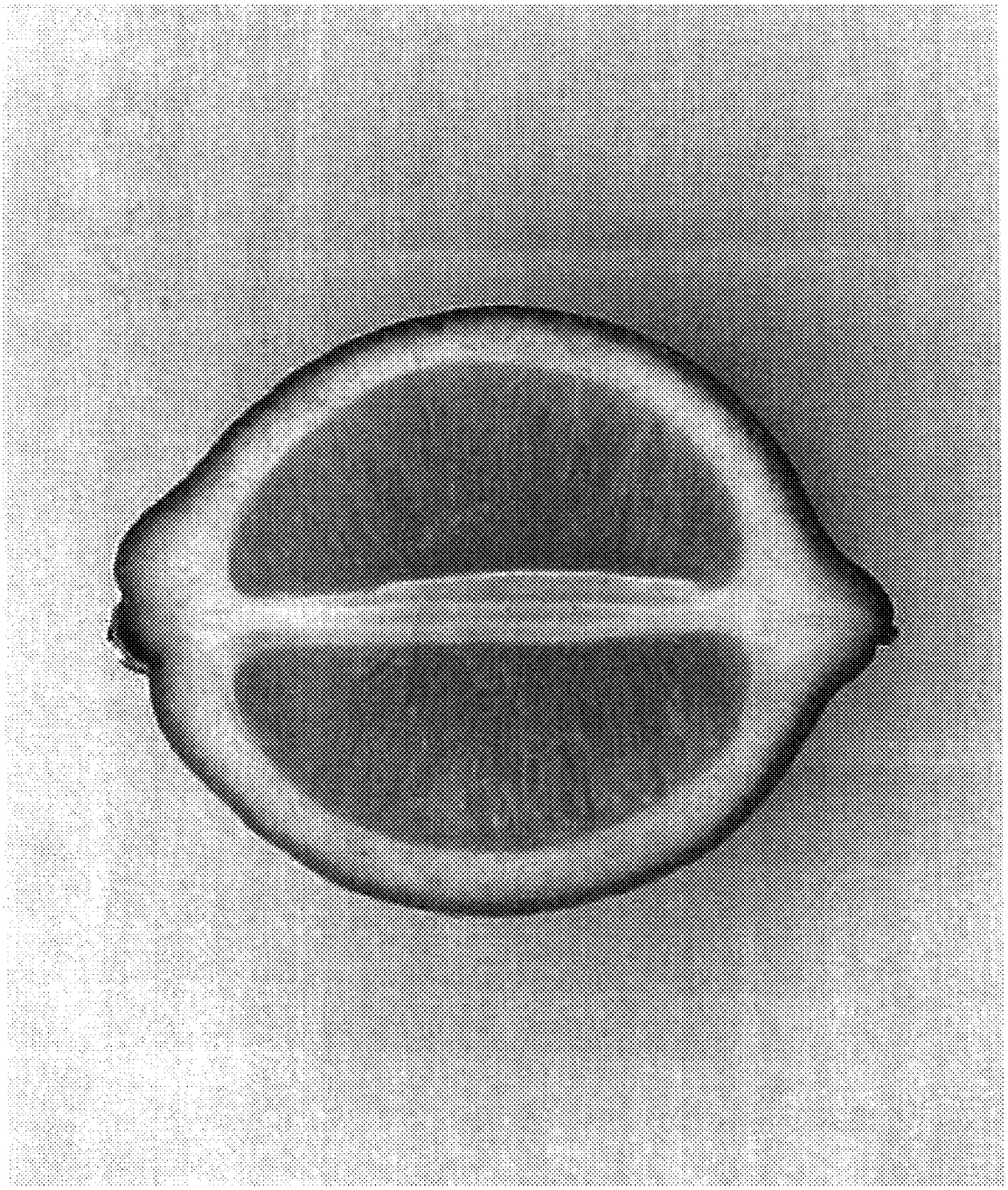
FIG. 4 is a color photograph showing a typical longitudinal cut section of fruit of the present invention.
Figure 5:
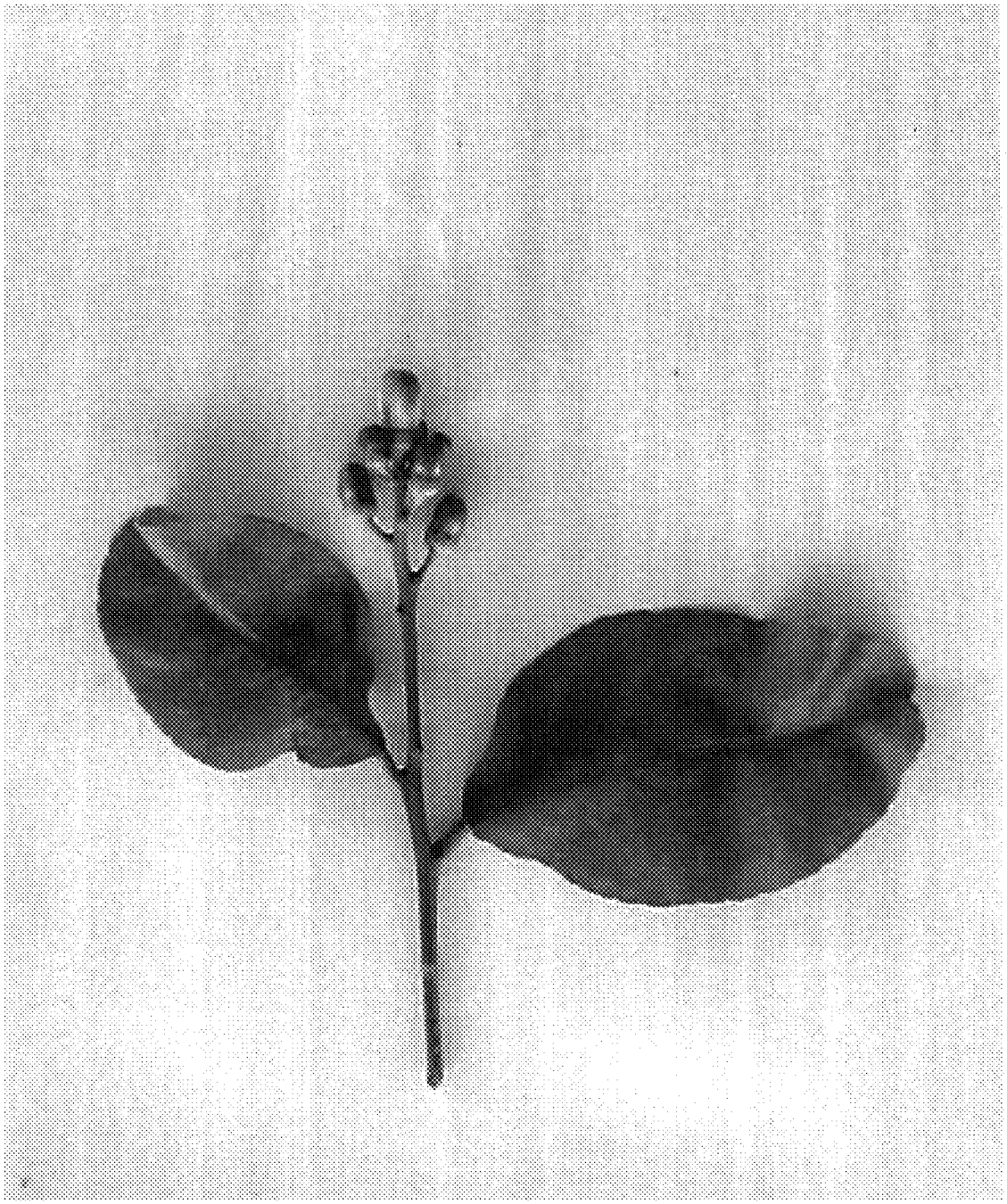
FIG. 5 is a color photograph showing a typical terminal branch bloom development and leaf morphology for the present invention.
Figure 6:
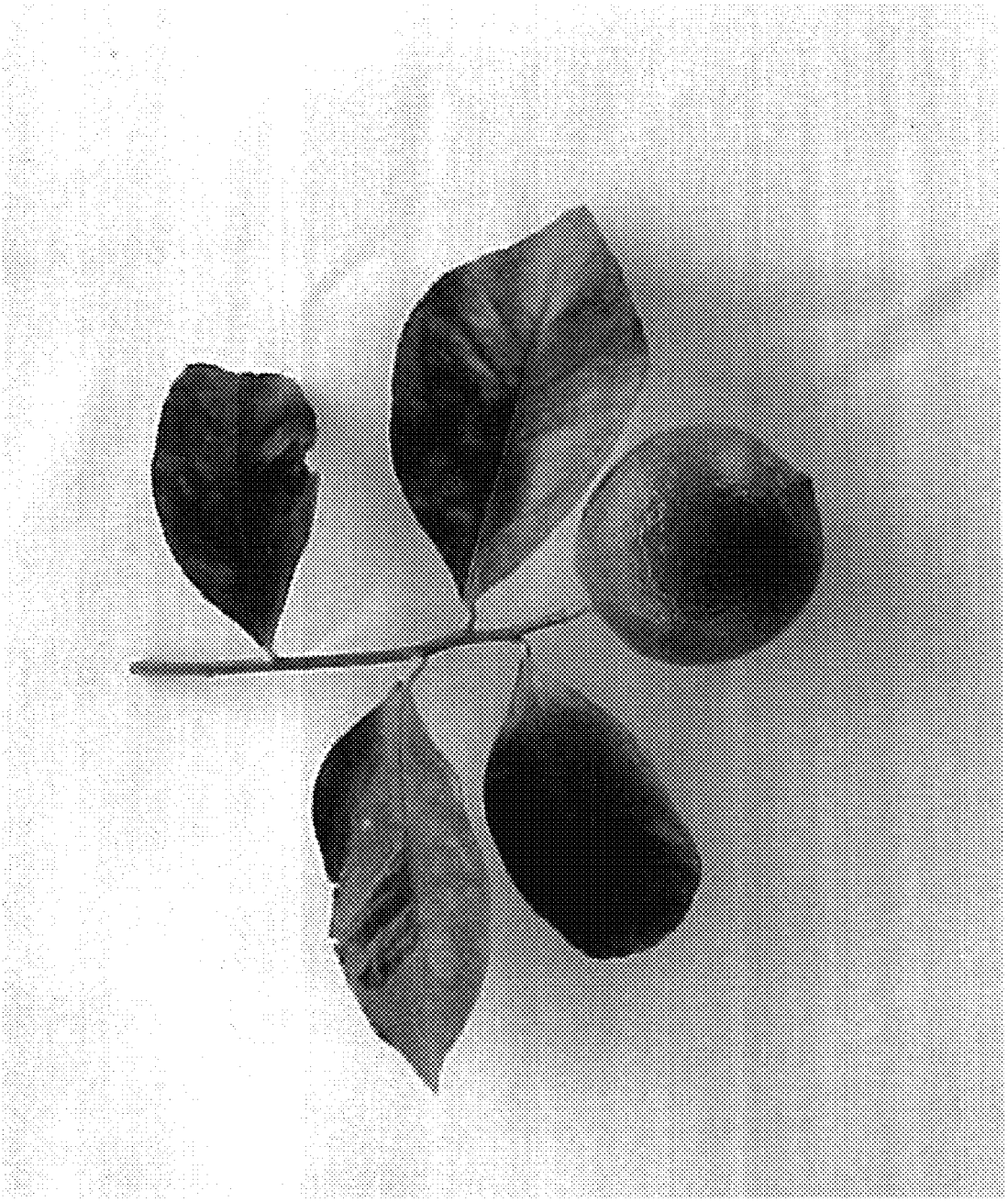
FIG. 6 is a color photograph showing a typical terminal fruit development of the present invention.
Figure 7:
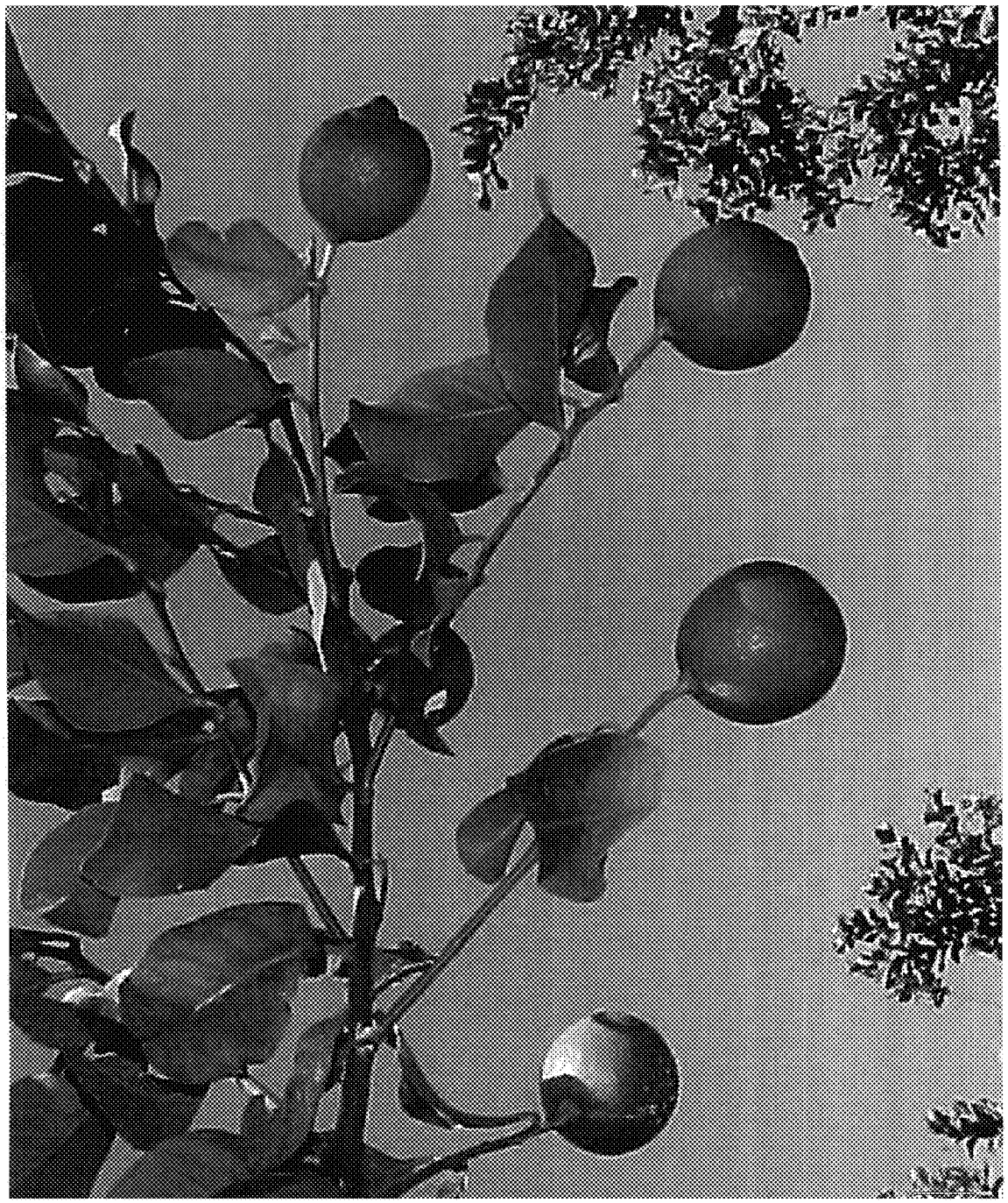
FIG. 7 is another color photograph showing a typical terminal fruit development of the present invention.
Figure 8:
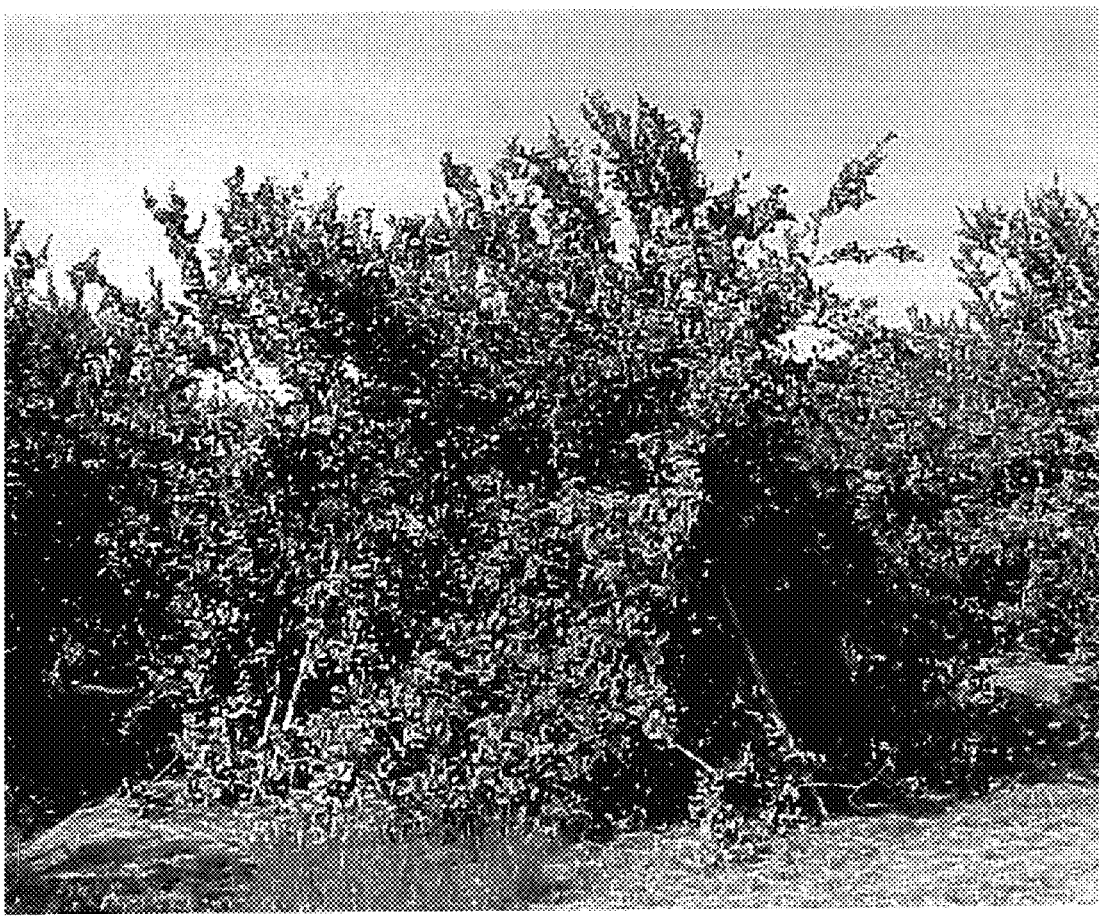
FIG. 8 is a color photograph showing the appearance of a whole tree of the present invention during the fall.
Figure 10:
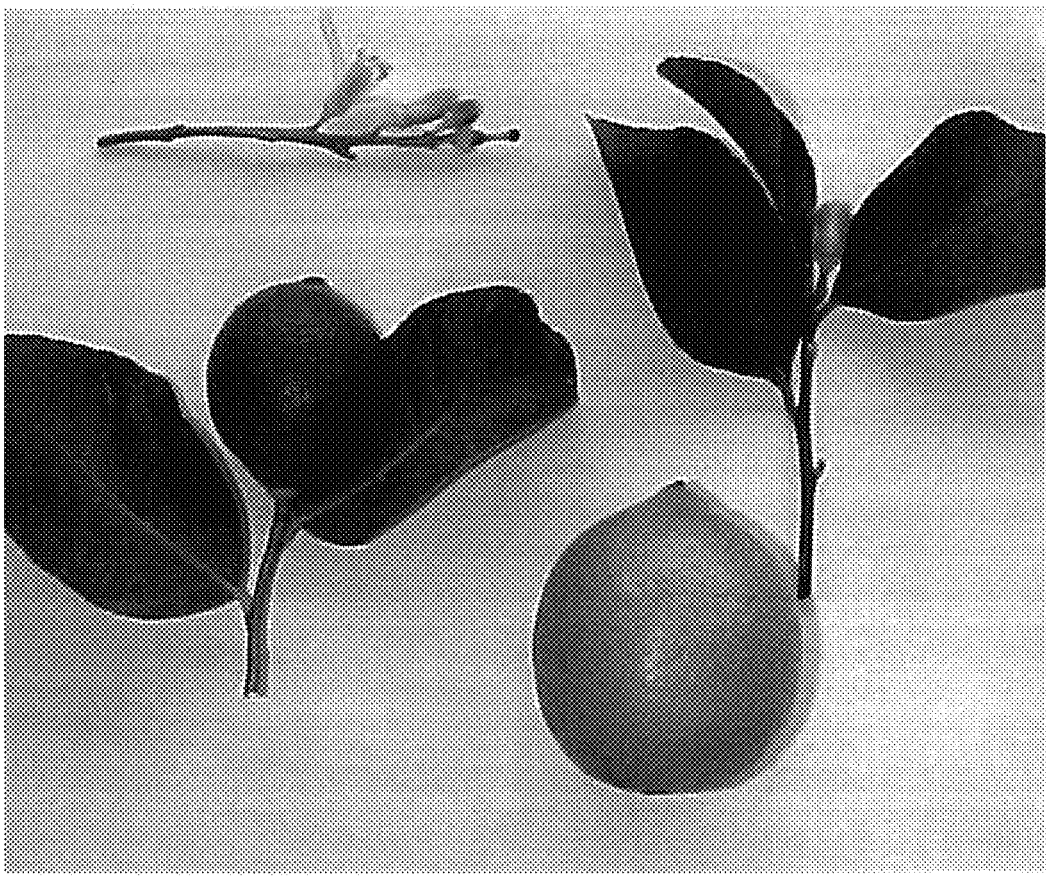
FIG. 10 is a color composite photograph showing various plant organs (fruit, leaves, flowers and stems) of the present invention as produced in California.
Figure 11:
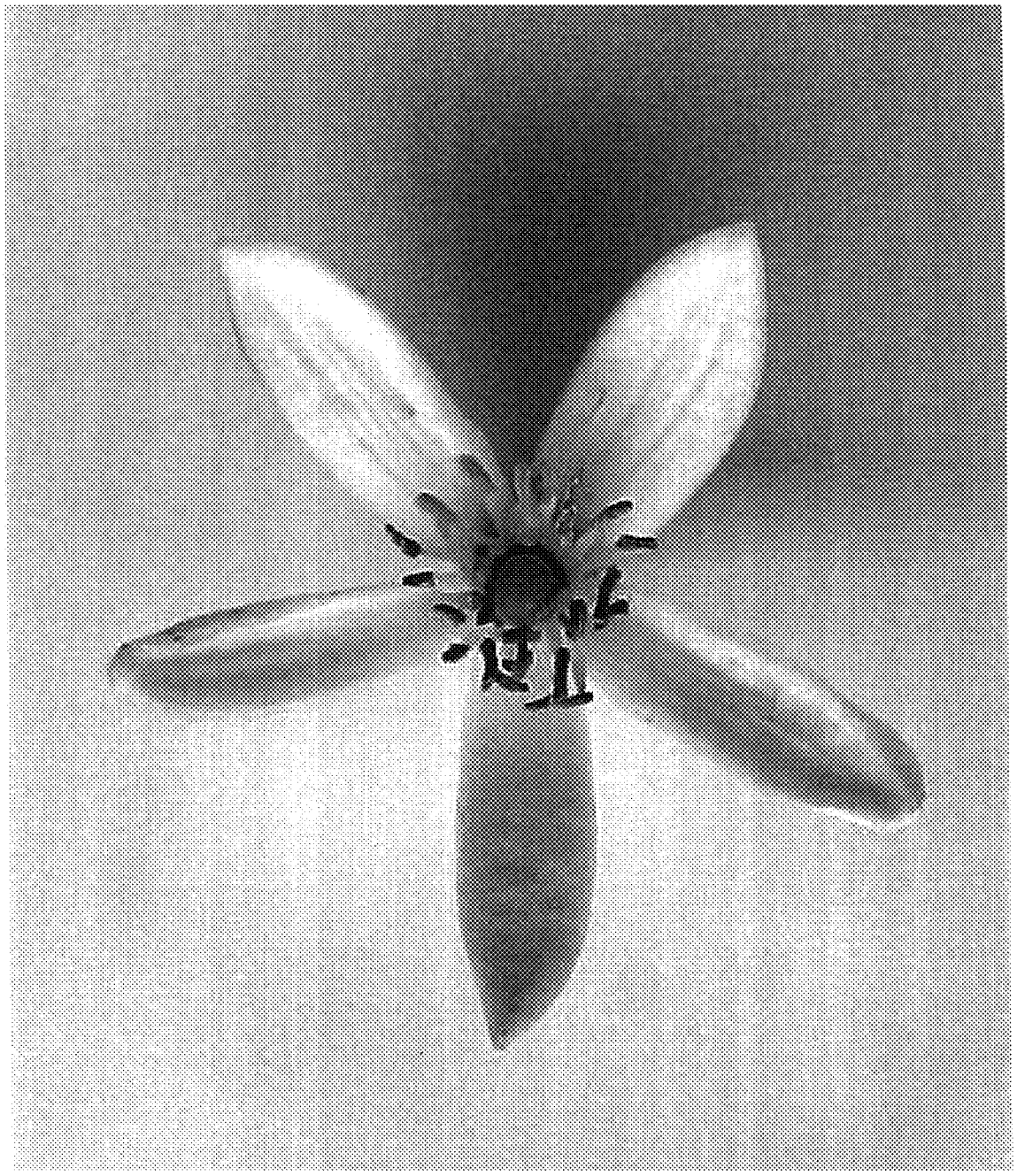
FIG. 11 is a color photograph of the present invention showing a fully open flower.
Figure 12:
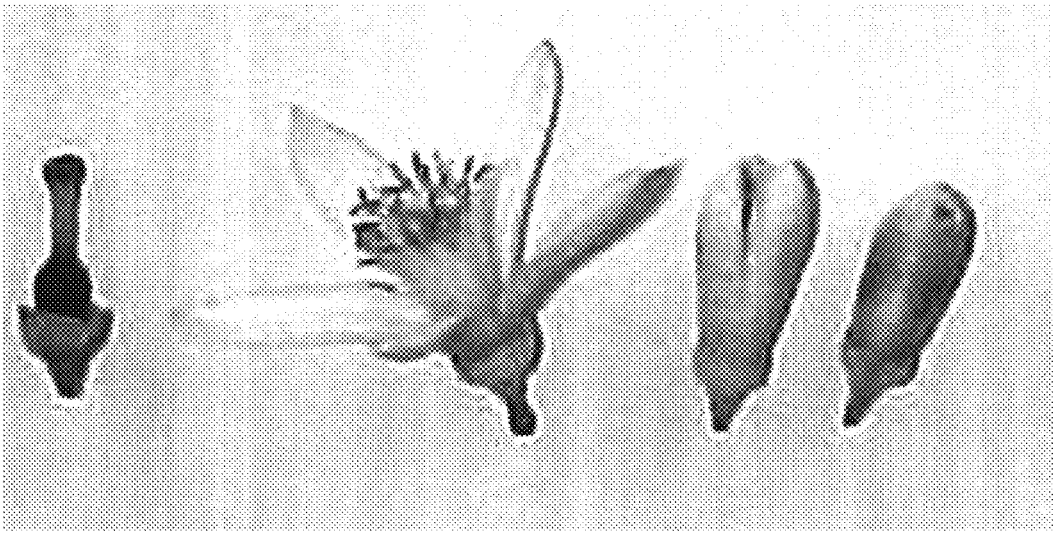
FIG. 12 is a color photograph of the present invention showing the various stages of floral development as well as color changes.
Figure 12:
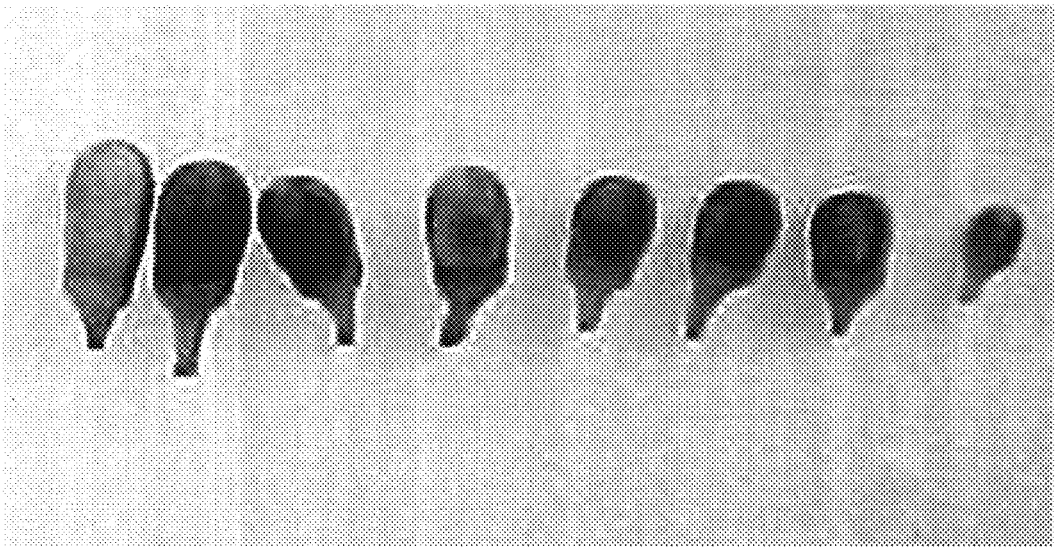

Flowers: Small — in clusters of three to five. See FIGS. 5 and 10.

*Diameter when fully opened.*—25–30 mm (1–1.2 in.).

*Bloom.*—E.g. quantity — abundant (typical of a lemon) non-alternate bearing.

Petals: 4–5, acute tips.

*Size.*—Medium to large (compared to other citrus species). Length: 12–18 mm (0.48–0.72 in.). Width: 6–8 mm (0.24–0.32 in.).

*Form.*—Narrow, linear, slightly oblong.

*Color.*—Adaxial surface — white (1-A-1). Abaxial surface — pink (2-F-6).

*Claws.*—None.

*Petal margins.*—Smooth, pointed at tips (acute).

*Pedicel.*—4–6 mm (0.16–0.24 in.) average. Color: Sea green (19-K-6).

*Sepals.*—Color: Calliste green (19-L-6). Shape: blunt at tips. Typical width at base: 5 mm (0.2 in.). Typical length: 2–3 mm (0.08–0.12 in.). Margin — smooth.

*Stamen.*—Number: 14–20, with completely style development. Filament: white (10-A-1). Anthers: 2–3 mm (0.08–0.12 in.) length; 1–2 mm (0.04–0.08 in.) width. Color: Aureolin$^{P}$ (10-L-2).

*Pistil.*—Stigma: ovoid shape, 3–4 mm (0.12–0.16 in.) diameter; Color: Pineapple (11-J-2). Style: 8–10 mm (0.32–0.4 in.) length; 2–3 mm (0.08–0.12 in.) wide; Color: Sea foam Y (17-C-2). Ovary: 6–8 mm (0.24–0.32 in.) diameter; ovoid shape; Color: Imperial jade (21-L-12).

FRUIT

On grafted trees the first fruit production occurred after two seasons. Internal characteristics: The fruit is commercially seedless in its normal cropping cycle. If the trees are manipulated to produce a summer flowering and hence a spring/summer crop (a Verdelli crop), then a low number of seeds may be present (less than 3 seeds per 15 fruit). Typical seed shape elliptical to ovoid. There is no persistence of the style on the fruit.

Internal characteristics:

Flesh color: Near rind, yellow (17-L-1); Remainder, yellow (17-L-1).

Interior segments: Average of 9 to 10 in number. Interior segment membranes — Thin.

Pulp vesicles: Medium, 6–8 mm (0.24–0.32 in.) length; 2 mm (0.08 in.) diameter; color: yellow (17-L-1).

The septa: Dorsal convex contoured character. Juice — abundant in mature fruit, evenly distributed in sections, typical lemon flavor: rich, with high acid and low sugar, well blended (pH of 3–3.7). The fruit center is complete without separation. Rind oil cells are medium to large, and occur at a density of approximately 30–50 per cm$^2$. Oil — 0.6–0.7% (approx. 655 g oil/100 kg fruit). Glandular layer 2–3 mm (0.08–0.12 in.). Mesocarp (albedo) — 5–8 mm (0.2–0.32 in.).

Axis: 5–6 mm (0.2–0.24 in.) diameter.

Fruit weight: Average of 110 g–130 g (mean of 100 fruit per tree and 5 trees).

Date of maturity: Southeast Turkey: about August 15$^{th}$. Riverside, Calif.: about August 25$^{th}$.

External characteristics:

Size: Medium.

*Length.*—60–70 mm (2.36–2.76 in.).

*Width.*—50–60 mm (1.97–2.36 in.).

Form: Round to slightly oval elliptical. Fruit surface — smooth. Basal (stem end) even to slightly raised.

Base: Diameter 12–14 mm (0.48–0.56 in.).

Stem: Length: 10–12 mm (0.4–0.48 in.).

Calyx: Diameter 5–8 mm (0.2–0.32 in.).

Apex: Slightly raised, distinctly nippled.

Aerole: Diameter 1–2 mm (0.04–0.08 in.).

Style scar: Yes, diameter 1–2 mm (0.04–0.08 in.).

Rind: Surface — smooth. Thickness — average 3–4 mm (0.12–0.16 in.). Color: Verdure (22-A-12) at first harvest (August) developing to a deep yellow (17-L-1) by the end of November. Internal fruit quality acceptability occurs approximately at the onset of temperature-induced color change. The fruit color changes to a bud green (19-K-10). At full color development the fruit has a uniform yellow hue (around 17-L-1).

The above description of this new variety of lemon is based on the growing conditions prevalent in the southeast area of Turkey and in Riverside, Calif. variations of the usual magnitude, such as differences in maturity date and production, may be due to cultural practices including irrigation, fertilization, pruning, fruit thinning and primary climate changes as well as soil conditions.

*Use.*—Fresh market/juice/oil extraction.

*Keeping quality.*—Excellent (stores for 6 months in controlled atmosphere.

*First harvest date.*—Around August 15$^{th}$ in southeast Turkey; around August 25$^{th}$ in Southern California Post harvest disorders are similar to existing lemon varieties. In post harvest storage trials under standard controlled atmosphere conditions, the 'Limoneira Seedless' could be economically stored, with minimal fruit loss for at least 6 months.

Table 1 below compares the fruit skin color, seeds and pollen fertility between fruit harvested from the 'Limoneira Seedless' as compared to 'Interdonato' on Sep. 14, 2002:

TABLE 1

| Tree | Fruit skin color (Sep. 14, 2002) | Seeds/fruit* (Sep. 14, 2002) | Pollen fertility** |
|---|---|---|---|
| Interdonato | Shamrock Gr (19-L-12) | 3–6 | 85% |
| Limoneira Seedless | Spring Gr (18-J-7) | <1 | 3–5% |

*100 fruit assessed per tree, 5 trees

**Estimated by acetocarmine staining during flowering in April

Table 2 details some preliminary yield data for grafted trees. Table 3 compares fruit juice and acid content for the 'Limoneira Seedless' lemon as compared to 'Interdonato' lemons for the 2002–2003 season. Measurements in each case were carried out on 10 fruit per tree and a 5 tree sample giving a total of a 50 fruit sample. Table 2 indicates the typical yield on grafted trees is as follows:

TABLE 2

| Typical Yield | |
|---|---|
| Year | Yield |
| Yr 1 | 0 |
| Yr 2 | 45 kg |
| Yr 3 | 95 kg |
| Yr 4 | 150 kg |

TABLE 3

| Fruit Acid | | | | |
|---|---|---|---|---|
| | 'Limoneira Seedless' | | 'Interdonato' | |
| Date | Acid (meq/100 g) | Juice % | Acid (meq/100 g) % | Juice |
| August 15th | 103 | 32 | 97 | 24 |
| August 30th | 107 | 31 | 101 | 25 |
| September 15th | 105 | 34.5 | 100 | 24.5 |
| September 30th | 111 | 36 | 107 | 26 |
| October 15th | 110 | 37.5 | 108 | 25 |
| October 30th | 112 | 38.5 | 110 | 27 |
| November 15th | 115 | 40 | 112 | 30 |
| November 30th | 114 | 41.5 | 117 | 32 |

TABLE 4

| Typical Picking Pattern of the 'Limoneira Seedless' Lemon in Adana, Turkey | | |
|---|---|---|
| First Pick: | 15–20% of total | Mid August |
| Second Pick | 30–40% of total | Mid October |
| Third Pick | 30% of total | Early December |
| Fourth Pick | 20% of total | February |

The Adana region of Turkey grows many similar varieties of citrus to those grown in California. As a comparison harvest times of certain common citrus varieties growing in the two regions are listed in Table 5 below:

TABLE 5

| Variety (all unpatented) | Adana, Turkey | Riverside, California (USA) |
|---|---|---|
| Meyer Lemon | week 36 to week 45 | week 38 to week 48 |
| Lisbon Lemon | week 38 to week 50 | week 40 to week 20* |
| Nules Clementine | week 46 to week 48 | week 43 to week 45 |
| Washington Navel | week 46 to week 50 | week 46 to week 52 |
| Minneola tangelo | week 50 to week 12* | week 1–week 14* |
| Valencia Orange | week 18 to week 24* | week 18 to week 28* |
| Limoneira Seedless Lemon | week 34 to week 16* | week 36 to week 20** |

*fruit is allowed to hang to the following year.
**Harvest time in the Southern Central Valley of California based on the harvest time of other citrus varieties.

What is claimed is:

1. A new and distinct variety of seedless lemon tree as described and illustrated that is characterized by early fruit production from about August through to about March in the inland citrus areas of South East Turkey and Riverside, Calif., the plant being capable of being induced to flower by irrigation stress in summer resulting in a late spring crop of lemons, the seedless fruit having typically ovoid shape, an average juice content of about 30% to about 40% at harvest, with smooth skin texture, and having acceptable rind thickness, acid-sugar ratios and color.

* * * * *